United States Patent
Dehdashtian et al.

[19]

[11] Patent Number: 6,024,729
[45] Date of Patent: Feb. 15, 2000

[54] HEMOSTASIS VALVE ASSEMBLY INCLUDING GUIDE WIRE SEAL

[75] Inventors: Mark Dehdashtian, Costa Mesa, Calif.; Gordon E. Atkinson, Cedarville, Ohio

[73] Assignees: Vernay Laboratories, Inc., Yellow Springs, Ohio; Baxter International Inc., Deerfield, Ill.

[21] Appl. No.: 09/038,500

[22] Filed: Mar. 10, 1998

[51] Int. Cl.[7] .................................................. A61M 5/00
[52] U.S. Cl. ........................................ 604/256; 604/167
[58] Field of Search ...................... 604/246, 256, 604/164, 158, 169, 167, 264; 137/846–850; 251/149.1

[56] References Cited

U.S. PATENT DOCUMENTS

| | | |
|---|---|---|
| 2,644,663 | 4/1953 | Klingler . |
| 3,067,425 | 11/1962 | Colley . |
| 3,422,844 | 1/1969 | Grise . |
| 4,133,457 | 1/1979 | Klassen . |
| 4,181,145 | 1/1980 | Mitchell . |
| 4,341,239 | 7/1982 | Atkinson ................................ 137/493 |
| 4,430,081 | 2/1984 | Timmermans ......................... 604/256 |
| 4,436,519 | 3/1984 | O'Neill ................................ 604/175 |
| 4,465,102 | 8/1984 | Rupp . |
| 4,524,805 | 6/1985 | Hoffman ................................ 137/846 |
| 4,535,819 | 8/1985 | Atkinson et al. ....................... 137/846 |
| 4,566,493 | 1/1986 | Edwards et al. ....................... 137/846 |
| 4,612,960 | 9/1986 | Edwards et al. ....................... 137/846 |
| 4,626,245 | 12/1986 | Weinstein . |
| 4,649,904 | 3/1987 | Krauter et al. ............................ 128/6 |
| 4,715,360 | 12/1987 | Akui et al. ................................ 128/4 |
| 4,752,287 | 6/1988 | Kurtz et al. . |
| 4,809,679 | 3/1989 | Shimonaka et al. . |
| 4,819,637 | 4/1989 | Dormandy, Jr. et al. . |
| 4,846,836 | 7/1989 | Reich . |
| 4,870,992 | 10/1989 | Irwin et al. . |
| 4,874,377 | 10/1989 | Newgard et al. . |
| 4,917,668 | 4/1990 | Haindl . |
| 4,929,235 | 5/1990 | Merry et al. ........................... 604/167 |
| 4,948,092 | 8/1990 | Kasper et al. . |
| 4,960,412 | 10/1990 | Fink ...................................... 604/167 |
| 5,000,745 | 3/1991 | Guest et al. . |
| 5,010,925 | 4/1991 | Atkinson et al. ...................... 137/847 |
| 5,041,095 | 8/1991 | Littrell ................................ 604/167 |
| 5,053,013 | 10/1991 | Ensminger et al. .................. 604/167 |
| 5,062,648 | 11/1991 | Gomringer . |
| 5,064,416 | 11/1991 | Newgard et al. . |
| 5,092,857 | 3/1992 | Fleischhacker . |
| 5,114,408 | 5/1992 | Fleischaker et al. ................. 604/167 |
| 5,125,903 | 6/1992 | McLaughlin et al. . |
| 5,137,024 | 8/1992 | Souma . |
| 5,141,498 | 8/1992 | Christian ............................ 604/167 |
| 5,176,652 | 1/1993 | Littrell ................................ 604/167 |
| 5,195,980 | 3/1993 | Catlin .................................. 604/167 |

(List continued on next page.)

FOREIGN PATENT DOCUMENTS

| | | |
|---|---|---|
| 515372 | 8/1955 | Canada . |
| 618205 | 4/1961 | Canada . |
| 0067007 | 5/1982 | European Pat. Off. . |
| 0157906 | 5/1982 | European Pat. Off. . |

(List continued on next page.)

*Primary Examiner*—Wynn Wood Coggins
*Assistant Examiner*—Deborah Blyveis
*Attorney, Agent, or Firm*—Biebel & French

[57] ABSTRACT

A hemostasis valve assembly adapted for use within a catheter introducer is disclosed. The valve assembly includes first, second and third sealing members wherein the second sealing member comprises a guide wire seal. The guide wire seal includes a plurality of lip members defining two pairs of diametrically opposed slits and an aperture intersecting at least one of the slits. The aperture is adapted to sealing engage a small diameter guide wire for preventing fluid flow out of the catheter introducer through the valve assembly, while the slits allow for the passage of a large diameter elongated member or catheter. Two pairs of diametrically opposed pre-load ribs extend radially towards the aperture for pressing the lip members together in sealing engagement. A substantially spherical inner surface is provided for guiding the guide wire to the aperture.

8 Claims, 7 Drawing Sheets

U.S. PATENT DOCUMENTS

| | | | |
|---|---|---|---|
| 5,197,955 | 3/1993 | Stephens et al. . | |
| 5,242,412 | 9/1993 | Blake, III . | |
| 5,242,413 | 9/1993 | Heiliger | 604/167 |
| 5,261,459 | 11/1993 | Atkinson et al. | 137/846 |
| 5,269,763 | 12/1993 | Boehmer et al. | 604/167 |
| 5,273,545 | 12/1993 | Hunt et al. . | |
| 5,273,546 | 12/1993 | McLaughlin et al. . | |
| 5,295,658 | 3/1994 | Atkinson et al. . | |
| 5,304,143 | 4/1994 | Green et al. | 604/167 |
| 5,312,363 | 5/1994 | Ryan et al. . | |
| 5,324,270 | 6/1994 | Kayan et al. . | |
| 5,330,437 | 7/1994 | Durman . | |
| 5,342,316 | 8/1994 | Wallace | 604/167 |
| 5,350,363 | 9/1994 | Goode et al. | 604/167 |
| 5,365,942 | 11/1994 | Shank . | |
| 5,385,552 | 1/1995 | Haber et al. . | |
| 5,391,153 | 2/1995 | Haber et al. . | |
| 5,395,352 | 3/1995 | Penny . | |
| 5,402,982 | 4/1995 | Atkinson et al. . | |
| 5,409,464 | 4/1995 | Villalobos . | |
| 5,437,646 | 8/1995 | Hunt et al. | 604/167 |
| 5,443,452 | 8/1995 | Hart et al. | 604/167 |
| 5,456,284 | 10/1995 | Ryan et al. | 137/522 |
| 5,496,280 | 3/1996 | Vandenbroek et al. . | |
| 5,514,098 | 5/1996 | Pfoslgraf et al. . | |
| 5,520,655 | 5/1996 | Davila et al. . | |
| 5,533,708 | 7/1996 | Atkinson et al. | 251/149.1 |
| 5,599,305 | 2/1997 | Hermann et al. | 604/95 |
| 5,643,227 | 7/1997 | Stevens . | |
| 5,709,664 | 1/1998 | Vandenbroek et al. . | |

FOREIGN PATENT DOCUMENTS

| | | |
|---|---|---|
| 0094813 | 5/1983 | European Pat. Off. . |
| 0139347 | 5/1984 | European Pat. Off. . |
| 0252890 | 7/1987 | European Pat. Off. . |
| 03088815 | 9/1988 | European Pat. Off. . |
| 0332884 | 2/1989 | European Pat. Off. . |
| 0336307 | 3/1989 | European Pat. Off. . |
| 0452045 | 4/1991 | European Pat. Off. . |
| 0499401 | 2/1992 | European Pat. Off. . |
| 0638290 | 7/1994 | European Pat. Off. . |
| 0692278 | 7/1995 | European Pat. Off. . |
| 3042229 | 11/1980 | Germany . |
| 3737121 | 11/1987 | Germany . |
| 3809127 | 3/1988 | Germany . |
| 2094443 | 2/1982 | United Kingdom . |
| 9302734 | 2/1993 | WIPO . |
| 9413987 | 6/1994 | WIPO . |
| 9810713 | 3/1998 | WIPO . |

HEMOSTASIS VALVE ASSEMBLY INCLUDING GUIDE WIRE SEAL

BACKGROUND OF THE INVENTION

1. Field of the Invention

The present invention relates generally to medical devices and, more particularly, to hemostasis valves for use within percutaneous catheter introducers.

2. Description of the Prior Art

The use of catheter introducers in percutaneous medical procedures is well known in the art. A catheter introducer typically includes a long sheath having a first end positioned within a vein or artery of a patient and a second end positioned immediately external to the epidermis of the patient. Since the control of bleeding is obviously essential when such catheter introducers are utilized, conventional catheter introducers include a hemostasis valve assembly positioned at the second end of the sheath to permit a loader, catheter or other medical instrument to be introduced into the body of the patient through the sheath while precluding blood from flowing out of the introducer.

In many percutaneous medical procedures, a small diameter guide wire is passed through the sheath of the introducer and inserted into a vein or artery. The guide wire serves as a guide for a large diameter loader, catheter or other medical instrument employed later in the procedure. It is therefore necessary for the valve assembly to provide a sufficient seal around the small diameter guide wire to prevent excessive blood loss through the introducer. However, the valve assembly must also allow passage of, and sealingly engage, the large diameter loader, catheter, or other medical instrument, so as to prevent the flow of blood through the introducer.

One type of valve commonly used to control the flow of blood is referred to as a "duckbill" valve. A conventional duckbill valve includes a pair of walls, each having a generally planar configuration, which converge and intersect along a line or slit. However, such duckbill valves are not well suited for use alone in catheter introducers where medical instruments are to be inserted through the valve. When an instrument is inserted into a conventional duckbill valve, it passes between the converging walls of the valve and through the slit. This causes the walls to separate and to create an undesirable flow channel between the slit and the instrument.

U.S. Pat. No. 4,929,235 discloses a catheter introducer valve assembly designed to overcome the limitations of the prior art duckbill valves. The valve assembly includes a first valve having a Y-shaped slit which seals off any flow of blood from the sheath of the introducer during the time a catheter tube is not present. A second valve, typically a disc seal with a small through-hole, seals around the catheter tube during and after the insertion of the catheter tube into the introducer so as to seal off any flow of blood.

The prior art catheter introducer valve assemblies have been successful in accomplishing the primary purpose of shutting off the flow of blood in the sheath when no medical instrument is present therein. Further, the prior art valve assemblies have been effective in allowing passage of and sealingly engaging the outer diameter of a catheter or other medical instrument.

However, the prior art catheter introducer valve assemblies have been unable to provide adequate seals around both a small diameter guide wire and large diameter medical instrument passing through the introducer. The prior art valve assemblies typically include a seal which is adapted to sealingly engage around the relatively large diameter medical instrument such that no seal is formed around a relatively small diameter guide wire. With further reference to U.S. Pat. No. 4,929,235, the through-hole of the second valve has a diameter adapted to sealingly engage a catheter or loader having a diameter typically of approximately 0.3 inches. A typical guide wire has a diameter of approximately 0.035 inches such that once the catheter or loader has been removed, leaving the guide wire alone within the valve assembly, a substantial gap exists between the second valve and the guide wire whereby blood may pass through the introducer.

Accordingly, there is a need for a catheter introducer valve assembly which provides for the effective sealing of blood flow during three separate and distinct conditions: when no medical instrument is inserted through the assembly, when a relatively large diameter medical instrument is inserted through the valve assembly, and when a relatively small diameter guide wire is inserted through the valve assembly. In addition, there is a need for a guide wire seal which provides an effective seal around the exterior of a guide wire which alone has been inserted through the valve assembly, but which also provides for the easy passage of a relatively large diameter catheter or loader.

SUMMARY OF THE INVENTION

The present invention provides a hemostasis valve assembly adapted for use within a catheter introducer. In a first mode of operation, the valve assembly seals blood from flowing through the catheter introducer when no instrument or device is passing therethrough. In a second mode of operation, the valve assembly seals around a relatively small diameter guide wire, while in a third mode of operation the valve assembly seals around a relatively large diameter elongated member or catheter. The valve assembly consistently and continuously seals off the flow of blood during all three modes of operation.

The valve assembly of the present invention comprises a valve body including first and second sealing members. The valve body defines a central passage having a longitudinal center axis and opposed inlet and outlet ends. The inlet end is adapted for introducing a guide wire and elongated member. The elongated member may comprise a loader or catheter, but is not limited thereto and may further comprise any conventional medical instrument used in percutaneous catheter introducers.

The first sealing member, or duckbill seal, includes a resilient body having a cylindrical support wall and a plurality of lip members extending radially inwardly from the support wall. The lip members are spaced circumferentially from each other and define at least one normally closed slit extending transversely to the central passage for preventing fluid flow out of the housing through the valve assembly.

The second sealing member, or guide wire seal, includes a resilient body having a cylindrical support wall and a plurality of radially extending lip members. The lip members are spaced circumferentially from each other and define at least one slit extending transversely to the central passage and an aperture coaxial with the longitudinal center axis. The aperture is adapted to sealingly engage the guide wire for preventing fluid flow out of the housing through the valve assembly when the guide wire is positioned within the second sealing member and the elongated member is absent from the second sealing member. At least one pre-load rib extends from the support wall towards the aperture for pressing at least two of the plurality of lip members together in sealing engagement. A substantially spherical inner surface opens toward the inlet end for guiding the guide wire to the aperture.

The valve assembly preferably further comprises a third sealing member, or catheter disc seal, including a resilient body having cylindrical support wall and a disc extending radially inwardly from the support wall. The disc defines an aperture coaxial with the longitudinal center axis and adapted to sealingly engage the elongated member for preventing fluid flow out of the housing through the valve assembly when the elongated member, or catheter is positioned within the third sealing member.

Therefore, it is an object of the present invention to provide a hemostasis valve assembly that effectively seals the flow of blood through the valve assembly when no medical instrument is inserted therethrough.

It is another object of the present invention to provide a valve assembly which seals off the flow of blood when no medical instrument is inserted therethrough and which also readily seals around medical instruments having a wide variety of diameters.

It is a further object of the invention to provide a guide wire seal which effectively seals about a relatively small diameter guide wire but also provides for the easy passage of a relatively large diameter medical instrument.

It is yet another object of the invention to provide a valve assembly which sealingly engages a relatively large diameter medical instrument, and which also upon removal of the instrument, sealingly engages a relatively small diameter guide wire thereby preventing the flow of blood through the valve assembly.

DETAILED DESCRIPTION OF THE PREFERRED EMBODIMENT

Figure 1:
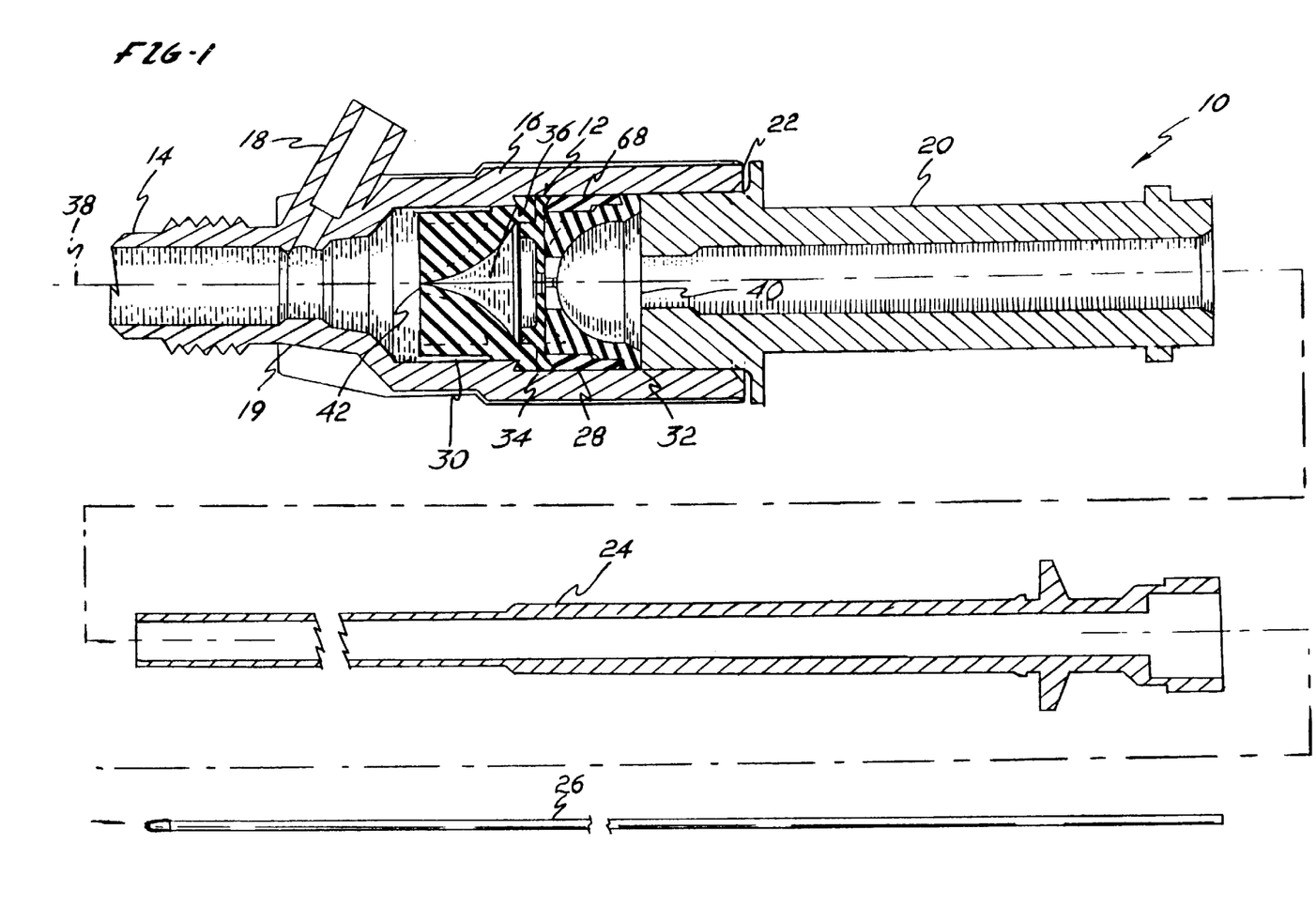
FIG. 1 is a cross-sectional view of a catheter introducer including the valve assembly of the present invention.

Referring initially to FIG. 1, a catheter introducer 10 is illustrated as including a hemostasis valve assembly 12, a sheath tube 14 and a housing 16. An angularly extending portion 18 is located adjacent a distal end 19 of the housing 16 and provides a means for introducing some material. e.g., a contrast or imaging medium, into the catheter introducer 10. The sheath tube 14 extends outwardly from the distal end 19 of the housing and is adapted to be introduced into the body of a patient in a manner as is known in the art. A locking cap 20 is received within a proximal end 22 of the housing 16 and locks the valve assembly 12 in both radial and axial position within the catheter introducer 10.

An elongated member, preferably a hollow loader or catheter 24, is adapted for introduction into the locking cap 20 and through the valve assembly 12 and sheath tube 14 for final positioning within a blood vessel of the patient. The catheter 24 typically has a relatively large outer diameter, or member diameter, in the order of 0.3 inches. The valve assembly 12 provides for the passage of and sealing engagement with the outer circumference of the catheter 24 thereby minimizing or preventing the loss of blood from the patient through the catheter introducer 10. A guide wire 26, having a relatively small outer diameter, or wire diameter, of approximately 0.035 inches, is adapted to be received within and pass through the catheter 24 into the blood vessel of the patient.

In conventional medical procedures, the catheter 24 is removed while the guide wire 26 remains in position within the patient's blood vessel. The valve assembly 12 also provides for sealing engagement with the outer surface of the guide wire 26 at this point in the procedure. The catheter 24, supporting a specialized medical instrument (not shown), such as a balloon catheter, is then reinserted through the valve assembly 12 of the catheter introducer 10. The catheter 24 passes through the sheath tube 14 while being guided over the guide wire 26 to a desired location within the patient's blood vessel. It should be noted that instead of the catheter 24 being reinserted through the valve assembly 12, an elongated member or medical instrument having an outer diameter intermediate the outer diameters of the catheter 24 and guide wire 26, is often substituted therefor.

The hemostasis valve assembly 12 comprises a valve body 28 including first, second and third sealing members 30, 32 and 34, respectively. The valve body 28 defines a central passage 36 having a longitudinal center axis 38 and opposed inlet and outlet ends 40 and 42. The inlet end 40 faces the proximal end 22 of the housing 16 and is adapted to receive the catheter 24 and guide wire 26. The outlet end 42 is positioned adjacent the distal end 19 of the housing 16.

Figure 2:
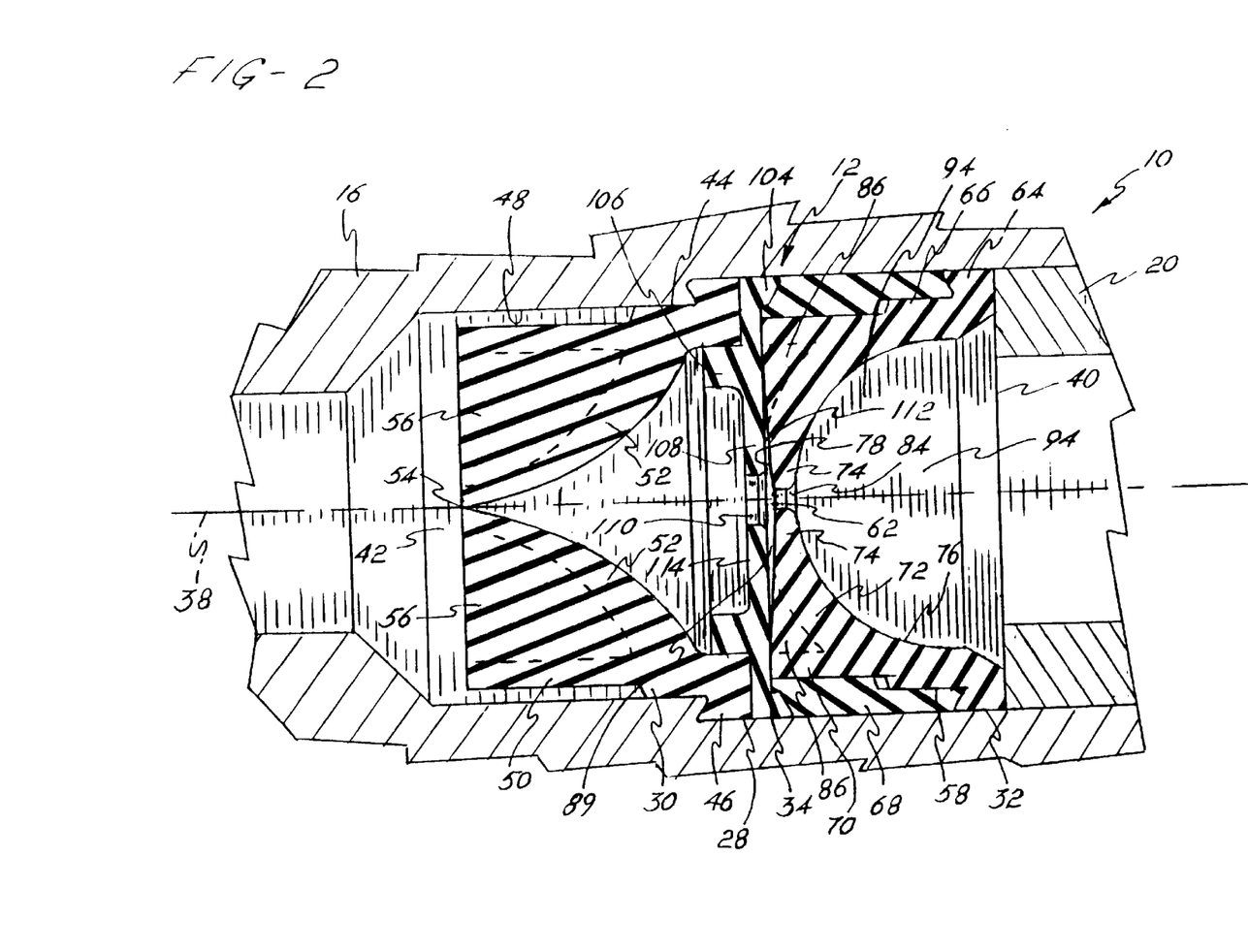
FIG. 2 is a cross-sectional view of the valve assembly of the present invention in a first mode of operation.
Figure 3:
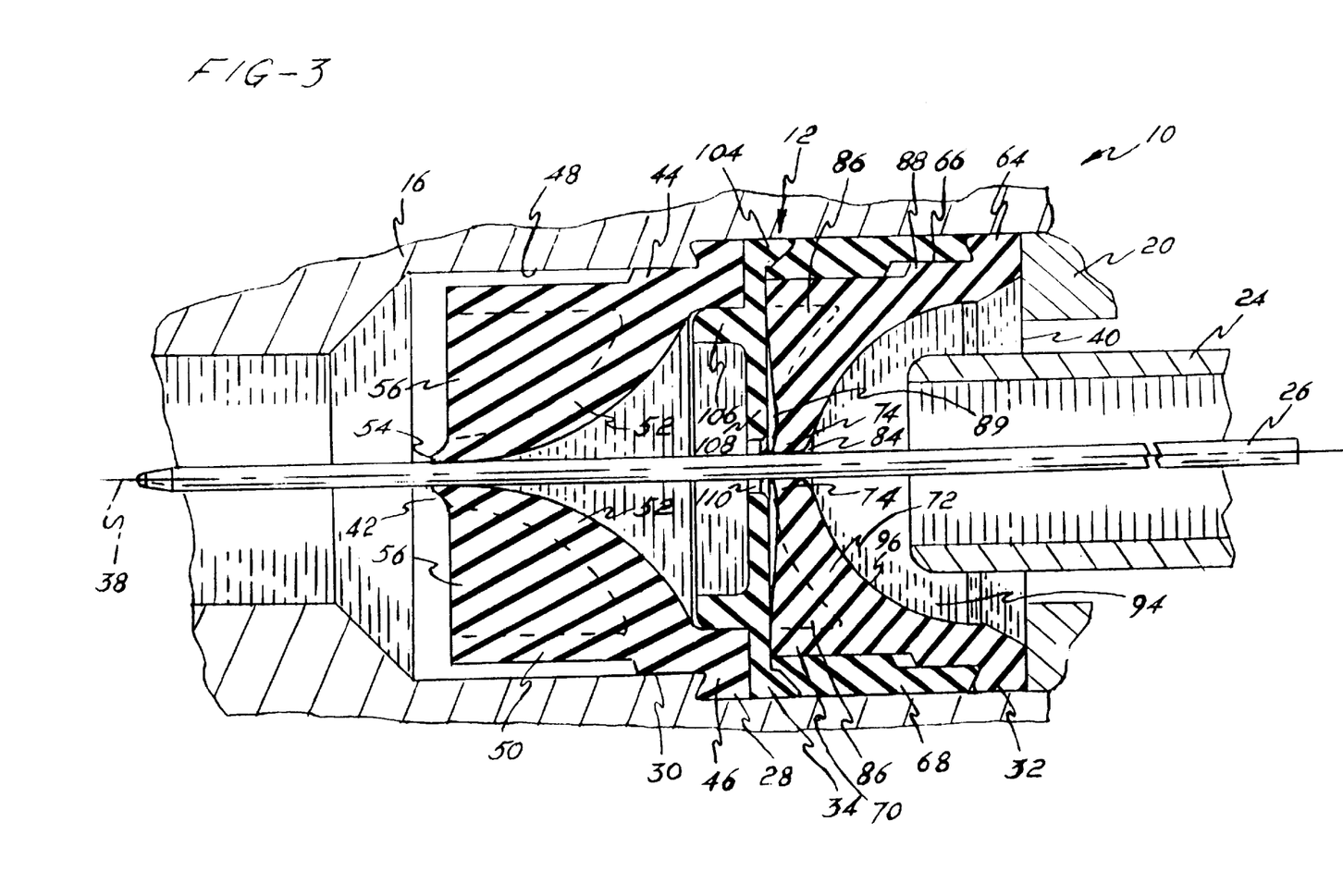
FIG. 3 is a cross-sectional view of the valve assembly of the present invention in a second mode of operation wherein a guide wire is positioned therein.
Figure 4:
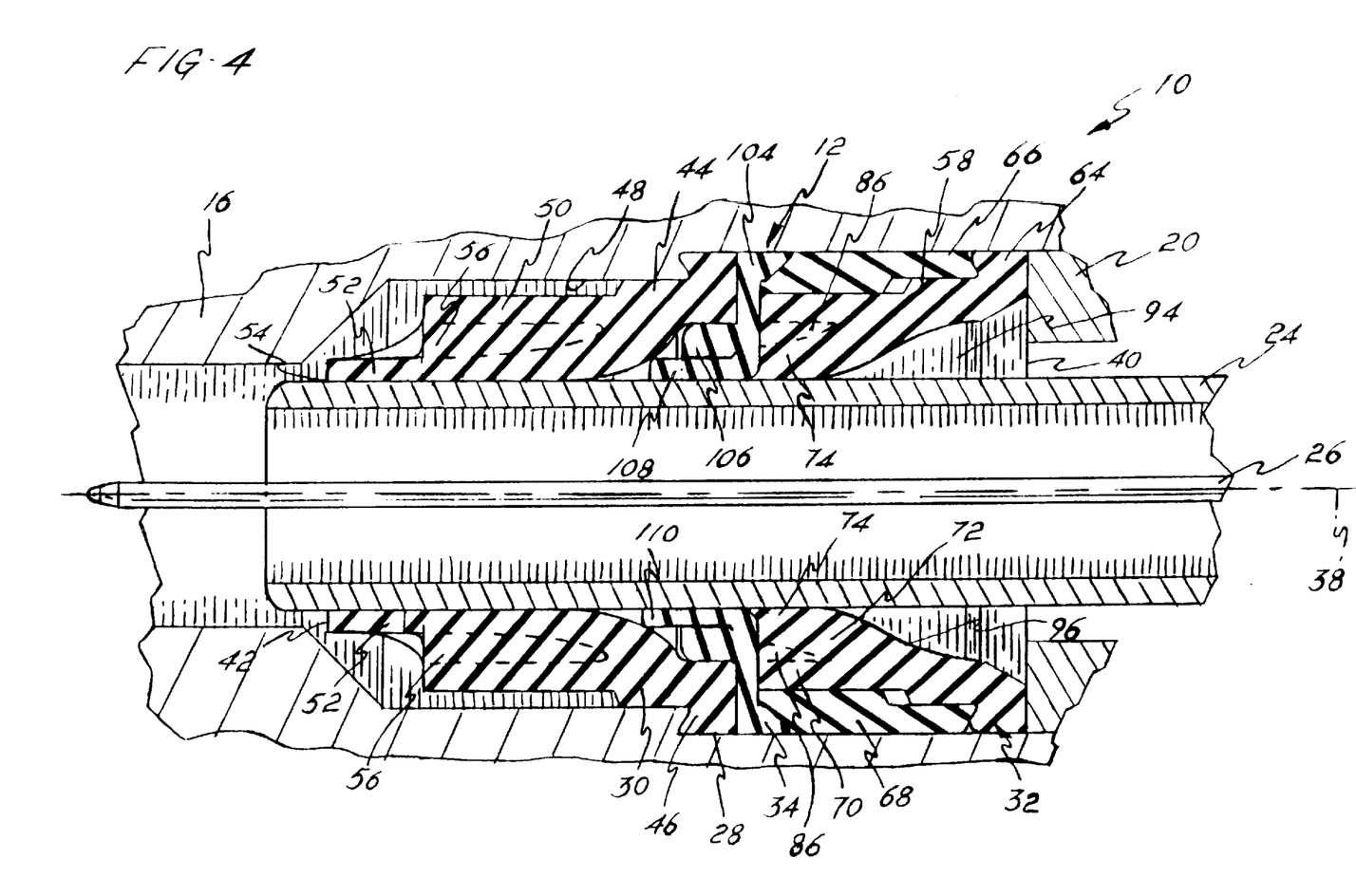
FIG. 4 is a cross-sectional view of the valve assembly of the present invention in a third mode of operation wherein a catheter is positioned therein.

As shown in FIG. 2, the first sealing member 30 is adapted to seal off any flow of blood through the catheter introducer 10 during the time that no medical instrument, including the catheter 24 and guide wire 26, are positioned within the valve assembly 12. The second sealing member 32 is adapted to seal off any blood flow through the catheter introducer 10 during the time in which the guide wire 26 alone is positioned within the valve assembly 12 as illustrated in FIG. 3. Turning now to FIG. 4, the third sealing member 34 is adapted to sealingly engage the outer circumference of the catheter 24 thereby preventing blood flow through the catheter introducer 10 when the catheter 24 is positioned within the valve assembly 12. It should be further noted that the third sealing member 34 is also adapted to sealingly engage the outer circumference of a medical instrument having a diameter intermediate that of the guide wire 26 and catheter 24. The second sealing member 32 is positioned between the first and third sealing members 30 and 34 such that the third sealing member 32 defines the inlet end 40 and the first sealing member 30 defines the outlet end 42 of the valve body 28.

Figure 5:
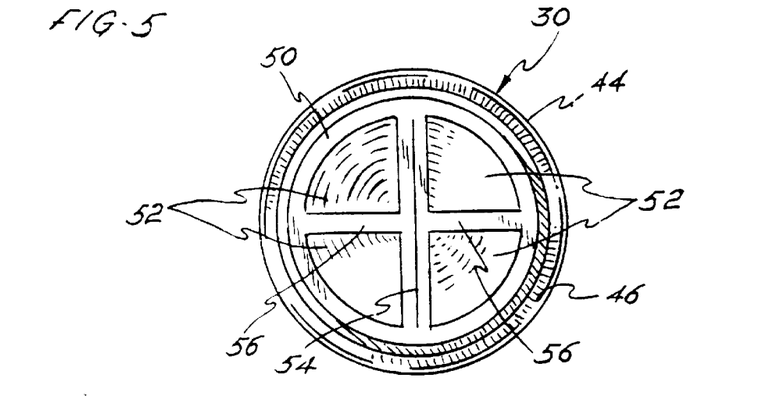
FIG. 5 is a top plan view of the duckbill seal of the valve assembly of the present invention.

Turning now to FIGS. 2 and 5, the first sealing member 30, or duckbill seal, includes a body 44 axially aligned with the center axis 38. The body 44 is preferably made of a flexible, resilient material such as polyisoprene or silicone. A mounting flange 46 is integrally formed as part of the body 44 for locating and sealingly engaging the inner surface 48 of the housing 16.

A cylindrical support wall 50 extends towards the outlet end 42 of the valve assembly 12 concentric with the mounting flange 46. A pair of lip members, preferably circumferentially spaced web members 52 extend radially inwardly from the cylindrical support wall 50 and axially outwardly towards the outlet end 42 to converge and form a normally closed slit 54. It should be apparent that the slit 54 forms what is known in the art as a duckbill seal 30.

Slit 54 is shown in its closed position in FIG. 2 and in its forced open position in FIGS. 3 and 4 wherein the guide wire 26 (FIG. 3) or catheter 24 (FIG. 4) is positioned between the web members 52 which have been pressed apart. In the closed position, increasing fluid pressure against the outlet end 42 of the web members 52 causes the slit 54 to remain firmly closed. When the guide wire 26 or catheter 24 is inserted from the inlet end 40, it will contact the edges of the web members 52 to cause the slit 54 to open and allow passage of the guide wire 26 or catheter 24. It should be noted that the web members 52 are capable of providing a large diameter opening whereby a catheter 24 or other medical instrument having an outer diameter proximate the inner diameter of the cylindrical support wall 50, may be inserted without tearing, stretching or otherwise damaging the duckbill seal 30.

A pair of diametrically opposed pre-load ribs 56 extend between the cylindrical support wall 50 and the slit 54 in a manner transverse, or perpendicular, to the slit 54. The pre-load ribs 56 in combination with the support wall 50 stiffen or rigidify the web members 52 to resist opening of the slit 54 by outward movement of the web members 52. In particular, radially outwardly acting forces are resisted by an inwardly acting reaction force produced by the pre-load ribs 56 being forced against the cylindrical support wall 50. This inwardly acting force results in the web members 52 being pressed together in a sealing relationship so that the leakage of blood is prevented or minimized. Further, the pre-load ribs 56 help to reliably close the web members 52 immediately after the withdrawal of the guide wire 26 or catheter 24 from the valve assembly 12.

Turning now to FIGS. 2 and 6–8, the second sealing member 32, or guide wire seal, includes a body 58 axially aligned with the center axis 38. The guide wire seal 32 includes an inlet end which defines the inlet end 40 of the valve assembly 12, and an outlet end 62. The body 58 preferably comprises a flexible, resilient material such as polyisoprene or silicone. First and second mounting flanges 64 and 66 are integrally formed as part of the body 58 wherein the first mounting flange 64 sealingly engages the inner surface 48 of the housing 16. The second mounting flange 66 sealing engages a cylindrical spacer 68 made of a material similar to that of the guide wire seal 32 (FIG. 2). The guide wire seal 32 is tightly positioned within the housing 16 between the third sealing member 34, spacer 68 and locking cap 20 such that axial and radial displacement of the guide wire seal 32 is prevented.

Figure 6:
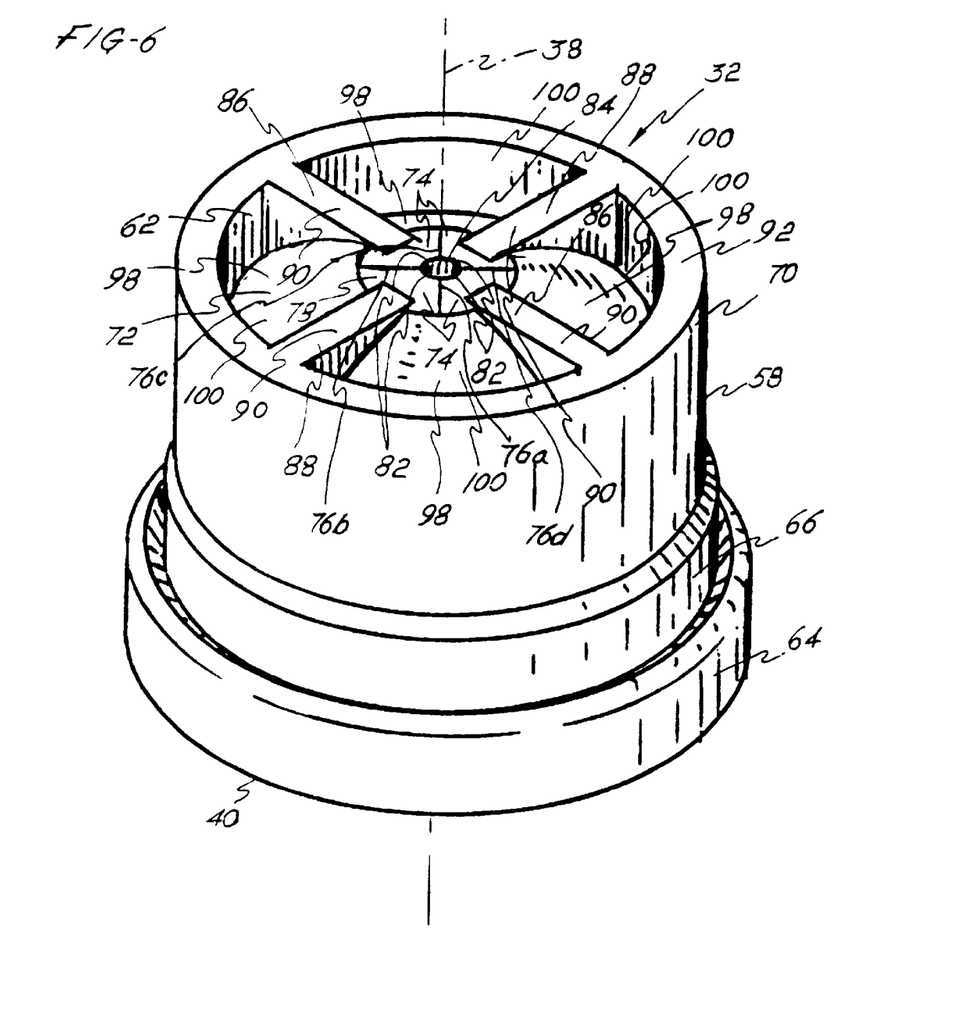
FIG. 6 is a perspective view of the guide wire seal of the present invention.
Figure 7:
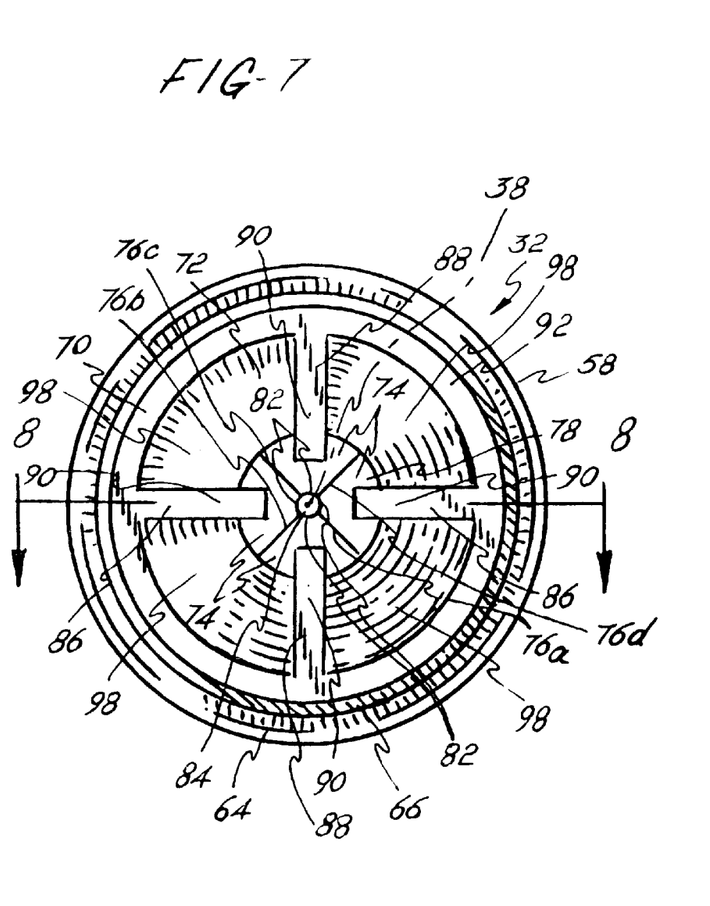
FIG. 7 is a top plan view of the guide wire seal of the present invention.
Figure 8:
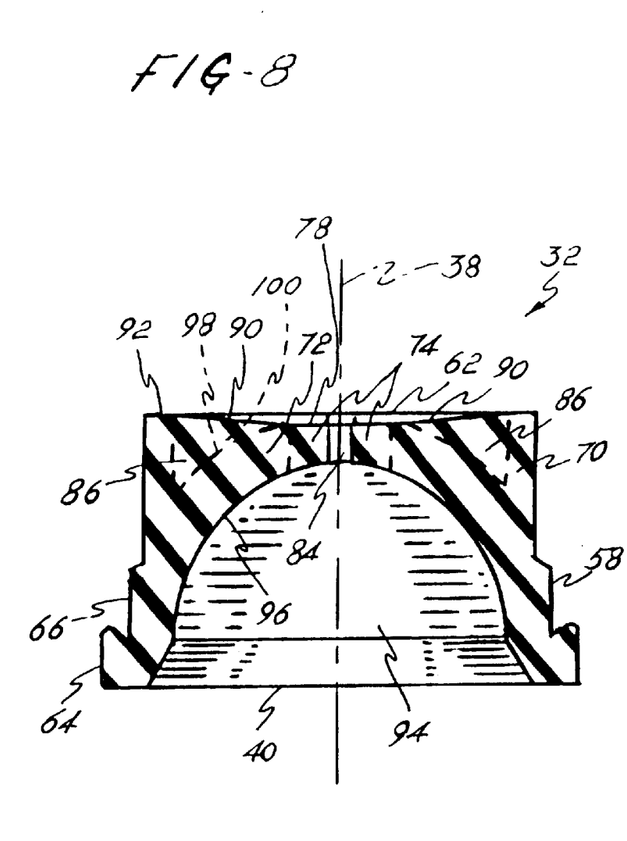
FIG. 8 is a cross-sectional view of the guide wire seal taken along line 8—8 of FIG. 7.

A cylindrical support wall 70 extends towards the outlet end 62 of the guide wire seal 32 concentrically to the mounting flanges 64 and 66. A disc 72 extends radially inwardly from the support wall 70 and includes lip members 74, four of which are presented for illustrative purposes in FIGS. 6 and 7. The lip members 74 extend in a direction radially outwardly from the center axis 38 and are circumferentially spaced an equal distance from each other. Each adjacent pair of lip members 74 converge to form a normally closed slit 76 at the outlet end 62 of the guide wire seal 32. As shown in FIGS. 6 and 7, four slits 76a, 76b, 76c and 76d are formed in the preferred embodiment. The lip members 74 combine to form a circular shaped planar surface 78 at the outlet end 62 and to define first and second pairs of diametrically opposed slits 76. More particularly, slits 76a and 76c define the first pair of diametrically opposed slits 76 while slits 76b and 76d form the second pair of diametrically opposed slits 76. In the preferred embodiment, the planar surface 78 has a diameter of approximately 0.2 inches such that each pair of diametrically opposed slits has a total width of approximately 0.2 inches. Each pair of slits 76a, 76c and 76b, 76d are radially aligned through the center axis 38. The slits 76 extend axially through the planar surface 78 and each pair of slits 76a, 76c and 76b, 76d are perpendicularly disposed to the other pair of slits 76b, 76d and 76a, 76c thereby forming a cross slit centered on axis 38.

The slits 76 are illustrated in their closed position in FIGS. 2 and 6–7 and in their forced open position in FIG. 4. In the closed position, the lip members 74 sealingly engage each other thereby closing the slits 76 and preventing blood from flowing therebetween. When the catheter 24 is inserted from the inlet end 60, it will contact the edges of the lip members 74 to cause the slits 76 to open and allow passage of the catheter 24. The lip members 74 are capable of providing a large diameter opening whereby the resilient body 58 permits a catheter 24 or other medical instrument having an outer diameter greater than the outer diameter of the circular planar surface 78 to be inserted without tearing, stretching or otherwise damaging the guide wire seal 32. Furthermore, because the diameter of the catheter 24 (0.3 inches) exceeds the maximum width of the pairs of slits 76 (0.2 inches), the guide wire seal 32 forms a fluid tight seal against the catheter 24 as it is extended therethrough.

Each lip member 74 includes an arcuate notch 82 which combine with the arcuate notches 82 of each adjacent lip member 74 to form a central aperture 84 coaxial with the longitudinal center axis 38. The aperture 84 has a circular cross-section and has a diameter which is approximately less than the outer diameter of the guide wire 26 or any other medical instrument or device which is arranged to be passed through the valve assembly 12. The aperture 84 therefore seals around the smallest diameter instrument or device, typically the guide wire 26, to be passed through the catheter introducer 10 and thereby minimize or prevent the outward flow of blood when such an instrument is present in the valve assembly 12. In the preferred embodiment, the aperture 84 has a diameter of approximately 0.033 inches to seal around a guide wire 26 of approximately 0.035 inches.

First and second pairs of diametrically opposed pre-load ribs 86 and 88 extend radially inwardly from the cylindrical support wall 70. The pre-load ribs 86 and 88 preferably extend radially inwardly into engagement with respective lip members 74, thereby optimizing resistance of the lip members 74 to movement such that adjacent lip members 74 tend to remain in sealing engagement and the slits 76 remain closed. The first pair of pre-load ribs 86 are disposed perpendicular to the second pair of pre-load ribs 88. Each pair of pre-load ribs 86 and 88 are preferably positioned at a predetermined angle, preferably 45°, to each adjacent slit 76 in order to facilitate sealing engagement of the lip members 74 as described below.

The pre-load ribs 86 and 88 preferably have a sloping or inclined upper surface 90 extending downwardly from the cylindrical support wall 70 toward the aperture 84. The angle of inclination of the upper surface 90 extending from proximate said aperture 84 toward the support wall 70 is preferably 5°. The inclined upper surface 90 provides for a clearance gap 89 (FIG. 2) between the second and third sealing members 32 and 34, thereby preventing the pre-load ribs 86 and 88 from substantially displacing the third sealing member 34 when the guide wire 26 alone is inserted therethrough as shown in FIG. 3. The outer end of the inclined upper surface 90 is level with the upper surface 92 of the support wall 70 while the inner end of the inclined upper surface 90 is level with the planar surface 78 of the disc 72.

The pre-load ribs 86 and 88 and support wall 70 stiffen or rigidify the disc 72 for resisting any force tending to open the slits 76 by outward movement of the lip members 74. In particular, the ribs 86 and 88 and support wall 70 hold the slits 76 together in sealing engagement to oppose blood pressure exerted against the outlet end 62. Additionally, the pre-load ribs 86 and 88 help to reliably close the lip members 74 immediately after withdrawal of the catheter 24 from the guide wire seal 32. Further, the pre-load ribs 86 and 88 help keep the slits 76 closed in sealing engagement as the guide wire 26 is passed through the aperture 84. An offset angle of 45° between the first and second pairs of pre-load ribs 86 and 88 and the first and second pairs of slits 76a, 76c and 76b, 76d, respectively, optimizes the resistance against any force tending to open the lip members 74.

The guide wire seal 32 includes a substantially spherical recess 94 which opens toward the inlet end 40 for guiding the tip of the guide wire 26 or catheter 24 to the aperture 84 during their introduction into the catheter assembly 12. The valve disc 72 has opposed inner and outer surfaces 96 and 98 oriented towards the inlet and outlet ends 60 and 62, respectively. The inner surface 96 is substantially spherical from proximate the inlet end 40 to the aperture 84, thereby defining the recess 94. By the spherical inner surface 96 extending radially inwardly up to the aperture 84, the guide wire 26 is guided through the aperture 84 in sealing engagement therewith without the tip of the guide wire 26 tending to contact and force open the slits 76 between adjacent lip members 74. The outer surface 98 is substantially spherical from the support wall 70 to the planar surface 78 thereby forming a plurality of arced recesses 100 between adjacent pre-load ribs 86 and 88 (FIG. 6).

Figure 9:
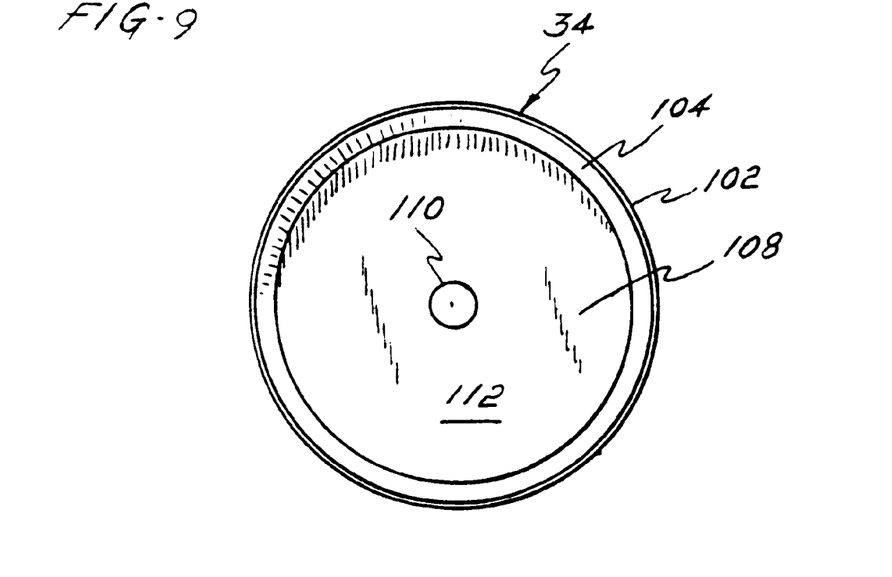
FIG. 9 is a bottom plan view of a catheter disc seal of the valve assembly of the present invention.
Figure 10:
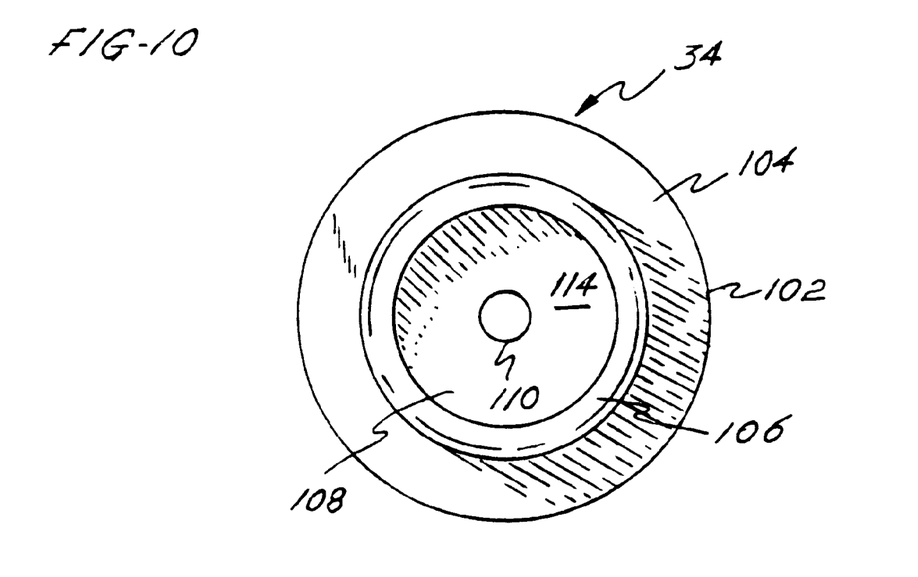
FIG. 10 is a top plan view thereof.

Turning now to FIGS. 2 and 9–10, the third sealing member 34, or catheter disc seal, is positioned in sealing engagement between the duckbill seal 30 and the guide wire seal 32. Again, the catheter disc seal 34 includes a body 102 preferably made of a flexible, resilient material such as polyisoprene or silicone. A mounting flange 104 is integrally formed as part of the body 102 wherein the flange 104 sealingly engages the inner surface 48 of the housing 16. As illustrated in FIG. 2, the catheter disc seal 34 is tightly positioned within the housing 16 between the guide wire seal 32, spacer 68 and duckbill seal 30 such that axial and radial displacement of the catheter disc seal 34 is prevented.

The body 102 includes a cylindrical support wall 106 and a disc 108 extending radially inwardly from the support wall 106. The disc 108 is formed with an aperture 110 coaxial with the longitudinal center axis 38. The aperture 110 has a diameter which is substantially greater than the outer diameter of the guide wire 26 but which is less than the outer diameter of the catheter 24 for sealing engagement between the disc 108 and the catheter 24. In the preferred embodiment, the diameter of the aperture 110 equals approximately 0.075 inches. The disc 108 has substantially planar inner and outer surfaces 112 and 114, respectively. It has been discovered that the addition of the catheter seal 34 assists in sealing around medical instruments passed through the valve assembly 12 which have outer diameters intermediate the diameters of the aperture 110 and catheter 24.

FIGS. 2–4, illustrate three different modes of operation of the valve assembly 12 of the present invention. FIG. 2 shows a first mode of operation wherein no guide wire 26, catheter 24, nor any other medical instrument is inserted within the valve assembly 12. In this first mode, it is readily apparent that the apertures 84 and 110 are coaxially aligned and provide fluid communication between the catheter disc seal 34 and the guide wire seal 32. However, the web members 52 of the duckbill seal 30 close the slit 54 thereby preventing or minimizing the flow of blood from the outlet end 42 through the catheter introducer 10.

FIG. 3 illustrates the second mode of operation where the guide wire 26 alone is positioned within the valve assembly 12. In this mode, the guide wire seal 32 provides the primary seal around the outer surface of the guide wire 26 to prevent or minimize the flow of blood from the outlet end 42 through the catheter introducer 10. As noted above, the guide wire 26 has a relatively small diameter, typically about 0.035 inches, such that the relatively large diameter aperture 110 of the catheter disc seal 34 does not sealingly engage the outer surface of the guide wire 26. Further, the duckbill seal 30, as described above, only provides a partial seal around the guide wire 26. However, since the diameter of aperture 84 of the guide wire seal 32 is smaller than the outer diameter of the guide wire 26, sealing engagement occurs between the guide wire seal 32 and guide wire 26. The slits 76 are simultaneously pressed together in sealing engagement by the pre-load ribs 86 and 88.

The third mode of operation is defined by insertion of the catheter 24 into the valve assembly 12, as illustrated in FIG. 4. As described above, the catheter 24 typically has a relatively large outer diameter on the order of 0.3 inches. As the catheter 24 is guided over the guide wire 26 from the inlet end 40 towards the outlet end 42, the catheter 24 easily passes through the guide wire seal 32 in sealing engagement therewith due to the resilient body 58 and lip members 74. Since the diameter of the catheter 24 exceeds the maximum width of the opening defined by the pairs of slits 76 of the guide wire seal 32 and the diameter of the aperture 110 of the catheter disc seal 34, both the guide wire and catheter disc seals 32 and 34 form fluid-tight seals against the catheter 24 when passed through the valve assembly 12.

As may be appreciated, the opening of the slits 76 may provide limited fluid communication between the guide wire seal 32 and catheter disc seal 34 if a medical instrument having an outer diameter intermediate the diameter of the guide wire 26 and the width of the pairs of slits 76 is inserted through the valve assembly 12. In such a case, where the medical instrument has an outer diameter greater than the diameter of the aperture 110, the catheter disc seal 34 provides the primary seal around the outer surface of the medical instrument.

From the above description, it should be apparent that the present invention provides for a hemostasis valve assembly adapted to be received within a catheter introducer. The valve assembly continuously seals blood from passing through the introducer. More particularly, the valve assembly seals the flow of blood when no instrument is inserted through the assembly when a relatively small diameter guide wire is passed through the assembly and when a relatively large diameter catheter is received within the assembly.

Further, the valve assembly includes a guide wire seal adapted for sealing engaging the guide wire while providing for the easy passage of the catheter.

While the forms of apparatus herein described constitute preferred embodiments of the invention, it is to be understood that the invention is not limited to these precise forms of apparatus and that changes may be made therein without departing from the scope of the invention which is defined in the appended claims.

What is claimed is:

1. A guide wire seal comprising:

a resilient body defining a longitudinal center axis and having inlet and outlet ends, said body including a cylindrical support wall, a plurality of radially extending lip members spaced circumferentially from each other, and first and second pairs of diametrically opposed pre-load ribs extending radially inwardly from said support wall;

said lip members defining first and second pairs of diametrically opposed slits and an aperture, said aperture coaxial with said longitudinal center axis and adapted to sealingly engage a guide wire having a wire diameter for preventing fluid flow through said guide wire seal when the guide wire alone is positioned within said guide wire seal;

said slits intersecting said aperture and adapted to allow passage of an elongated member having a member diameter greater than the wire diameter; and wherein said first and second pairs of pre-load ribs are offset from said first and second pairs of slits by a predetermined angle.

2. The guide wire seal of claim 1 wherein said predetermined angle by which said first and second pairs of pre-load ribs are offset from said first and second pairs of slits equals 45 degrees.

3. The guide wire seal of claim 2 wherein said first and second pairs of diametrically opposed pre-load ribs extend radially inwardly from said support wall into engagement with said lip members thereby forcing each of said lip members into sealing engagement with adjacent said lip members.

4. A guide wire seal comprising:

a resilient body defining a longitudinal center axis and having inlet and outlet ends, said body including a cylindrical support wall, a plurality of radially extending lip members spaced circumferentially from each other, and first and second pairs of diametrically opposed pre-load ribs extending radially inwardly from said support wall;

said lip members defining first and second pairs of diametrically opposed slits and an aperture, said aperture coaxial with said longitudinal center axis and adapted to sealingly engage a guide wire having a wire diameter for preventing fluid flow through said guide wire seal when the guide wire alone is positioned within said guide wire seal;

said slits intersecting said aperture and adapted to allow passage of an elongated member having a member diameter greater than the wire diameter; and wherein each of said ribs includes an inclined upper surface extending downwardly from said support wall toward said aperture.

5. The guide wire seal of claim 4 wherein said inclined upper surface has an angle of inclination of 5 degrees extending from proximate said aperture toward said support wall.

6. The guide wire seal of claim 5 wherein said first and second pairs of diametrically opposed pre-load ribs extend radially inwardly from said support wall into engagement with said lip members thereby forcing each of said lip members into sealing engagement with adjacent said lip members.

7. A guide wire seal comprising:

a resilient body defining a longitudinal center axis and having inlet and outlet ends, said body including a cylindrical support wall, a plurality of radially extending lip members spaced circumferentially from each other, and first and second pairs of diametrically opposed pre-load ribs extending radially inwardly from said support wall;

said lip members defining first and second pairs of diametrically opposed slits and an aperture, said aperture coaxial with said longitudinal center axis and adapted to sealingly engage a guide wire having a wire diameter for preventing fluid flow through said guide wire seal when the guide wire alone is positioned within said guide wire seal;

said slits intersecting said aperture and adapted to allow passage of an elongated member having a member diameter greater than the wire diameter; and wherein said body further comprises a substantially spherical inner surface which extends from said aperture and opens toward said inlet end for guiding the guide wire to said aperture.

8. A guide wire seal comprising:

a resilient body defining a longitudinal center axis and having inlet and outlet ends, said body including a cylindrical support wall, a disc concentrically disposed inside said support wall and including a plurality of radially extending lip members spaced circumferentially from each other, and first and second pairs of pre-load ribs extending radially inwardly from said support wall into engagement with said lip members;

said lip members defining first and second pairs of diametrically opposed slits and an aperture, said aperture coaxial with said longitudinal center axis and adapted to sealingly engage a guide wire having a wire diameter for preventing fluid flow through said guide wire seal when the guide wire alone is positioned within said guide wire seal;

said slits intersecting said aperture and adapted to allow passage of an elongated member having a member diameter greater than the wire diameter; and wherein said first and second pairs of pre-load ribs force each of said lip members into sealing engagement with adjacent said lip members.

* * * * *